US009242022B2

(12) United States Patent
Asmus et al.

(10) Patent No.: US 9,242,022 B2
(45) Date of Patent: Jan. 26, 2016

(54) HYDROGELS WITH TAPERED EDGE

(75) Inventors: Robert A. Asmus, Hudson, WI (US);
David R. Holm, Hudson, WI (US);
Daniel T. Popko, Stillwater, MN (US);
Richard L. Jacobson, Stillwater, MN (US); Terrance M. Smorch, Lake Elmo, MN (US); Donald G. Peterson, Shoreview, MN (US); Steven B. Heinecke, New Richmond, WI (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 983 days.

(21) Appl. No.: 12/352,189

(22) Filed: Jan. 12, 2009

(65) Prior Publication Data
US 2009/0187130 A1 Jul. 23, 2009

Related U.S. Application Data

(60) Provisional application No. 61/022,036, filed on Jan. 18, 2008.

(51) Int. Cl.
*A61K 9/70* (2006.01)
*A61L 15/60* (2006.01)
*A61L 15/46* (2006.01)
*A61L 15/58* (2006.01)

(52) U.S. Cl.
CPC ............... *A61L 15/60* (2013.01); *A61L 15/46* (2013.01); *A61L 15/58* (2013.01); *A61L 2300/206* (2013.01); *A61L 2300/404* (2013.01)

(58) Field of Classification Search
None
See application file for complete search history.

(56) References Cited

U.S. PATENT DOCUMENTS

| | | |
|---|---|---|
| RE24,906 E | 12/1960 | Ulrich |
| 3,389,827 A | 6/1968 | Abere et al. |
| 3,645,835 A | 2/1972 | Hodgson |
| 4,112,213 A | 9/1978 | Waldman |
| 4,310,509 A | 1/1982 | Berglund |
| 4,323,557 A | 4/1982 | Rosso et al. |
| 4,366,814 A | 1/1983 | Riedel |
| 4,472,480 A | 9/1984 | Olson |
| 4,737,410 A | 4/1988 | Kantner |
| 4,867,742 A | 9/1989 | Calderon |
| 4,867,748 A | 9/1989 | Samuelsen |
| 4,909,244 A | 3/1990 | Quarfoot et al. |
| 4,931,282 A | 6/1990 | Asmus et al. |
| 5,059,424 A | 10/1991 | Cartmell et al. |
| 5,088,483 A | 2/1992 | Heinecke |
| 5,106,629 A | 4/1992 | Cartmell et al. |
| 5,133,821 A | 7/1992 | Jensen |
| 5,160,315 A | 11/1992 | Heinecke et al. |
| 5,225,473 A | 7/1993 | Duan |
| 5,270,358 A * | 12/1993 | Asmus ............................ 524/55 |
| 5,276,079 A * | 1/1994 | Duan et al. ...................... 524/386 |
| 5,338,490 A * | 8/1994 | Dietz et al. ...................... 252/500 |
| 5,389,376 A | 2/1995 | Duan et al. |
| 5,409,966 A | 4/1995 | Duan et al. |
| 5,423,737 A | 6/1995 | Cartmell et al. |
| 5,438,988 A * | 8/1995 | Duan et al. ...................... 600/391 |
| 5,447,492 A | 9/1995 | Cartmell et al. |
| 5,531,855 A | 7/1996 | Heinecke et al. |
| 5,714,225 A | 2/1998 | Hansen et al. |
| 6,264,976 B1 | 7/2001 | Heinecke et al. |
| 6,436,432 B2 | 8/2002 | Heinecke et al. |
| 6,838,589 B2 | 1/2005 | Liedtke et al. |
| 7,217,853 B2 | 5/2007 | Kulichikhin et al. |
| 2001/0031370 A1 | 10/2001 | Kundel |
| 2003/0125680 A1 | 7/2003 | Ding |
| 2004/0247654 A1 | 12/2004 | Asmus et al. |
| 2004/0247655 A1 | 12/2004 | Asmus et al. |
| 2006/0064049 A1 | 3/2006 | Marcussen |

FOREIGN PATENT DOCUMENTS

| | | | |
|---|---|---|---|
| EP | 0 318 183 A2 | 4/1989 | |
| EP | 0424165 | * 10/1990 | ............. A61F 13/02 |
| EP | 0919211 A2 | 11/1998 | |
| JP | H03-141229 | 6/1991 | |
| WO | WO0220067 | * 3/2002 | ............. A61L 15/24 |
| WO | WO0234304 | * 5/2002 | ............. A61L 15/32 |
| WO | WO 03/080133 | 10/2003 | |

* cited by examiner

*Primary Examiner* — Hasan Ahmed
(74) *Attorney, Agent, or Firm* — 3M Innovative Properties Company; Lynn R. Hunsberger

(57) ABSTRACT

An adhesive hydrogel dressing as well as to methods of applying the dressing to a patient is described. The dressing generally comprises an adhesive hydrogel pad, a backing layer, and an adhesive layer on the backing layer facing the hydrogel pad. The adhesive layer and backing layer form a perimeter around the hydrogel pad and hold the hydrogel pad in place on an application surface. The adhesive hydrogel pad is formed with at least a portion of the perimeter of the hydrogel pad tapered proximate the area that the hydrogel pad and release liner separate during liner removal.

44 Claims, 4 Drawing Sheets

HYDROGELS WITH TAPERED EDGE

CROSS-REFERENCE TO RELATED APPLICATION

This application claims priority to U.S. Provisional Patent Application No. 61/022,036, filed Jan. 18, 2008, the disclosure of which is incorporated by reference herein in its entirety.

BACKGROUND OF THE INVENTION

Hydrocolloid adhesive compositions that are formed as dressings have been known for many years. Typically, these compositions comprise a blend of a polymer matrix, such as a rubbery elastomer like polyisobutylene, in combination with one or more water-soluble or water-swellable hydrocolloids, such as a dry powdered mixture of pectin, gelatin and carboxymethylcellulose. The adhesive composition is usually coated on at least one surface of a water-insoluble film to form a relatively thick, heavy dressing.

Commercially available examples of hydrocolloid dressings include "DUODERM" and "DUODERM EXTRA-THIN" dressing (a product of Convatec; Squibb and Sons, Inc., Princeton, N.J.; 3M TEGADERM hydrocolloid dressing (a product of 3M Company, St. Paul, Minn.); RESTORE dressing (a product of Hollister, Inc., Libertyville, Ill.); and COMFEEL dressing (a product of Coloplast International, Espergaerde, Denmark). See, also, U.S. Pat. Nos. 4,909,244; 5,447,492; and 5,106,629.

The TEGASORB dressing has a thin, adhesive coated polymeric backing extending beyond the edges of the absorbent hydrocolloid pad to form a border that will adhere to the skin and provide a barrier to outside contamination as well as keep wound fluid contained providing for a longer wear time as described in U.S. Pat. Nos. 6,436,432 and 6,264,976. A carrier frame surrounds the perimeter of the dressing, providing sufficient support (e.g. rigidity) to the backing to facilitate handling of the dressing during application to a wound.

Several contoured hydrocolloid adhesives used as medical dressings are described in U.S. Pat. Nos. 4,867,742; 5,133,821 (a process for making by an in-line process a contoured hydrocolloid adhesive dressing);U.S. Pat. No. 7,217,853 (dressing or patch with a tapered edge); U.S Patent Publication No. 2003/0125680; and EP Patent No. 0919211 A2. Despite these advances, a need remains for conformable dressings, particularly in an island dressing format.

SUMMARY OF THE INVENTION

The invention provides an adhesive hydrogel island dressing and delivery system that facilitates removal of a release liner from the adhesive hydrogel dressing during application. An adhesive hydrogel pad is provided with at least a portion of the hydrogel pad's perimeter having a beveled, contoured, stepped or tapered edge. The tapered portion of the perimeter reduces the thickness of the adhesive hydrogel, typically in a progressive manner, in relation to the thickest part of the hydrogel pad. The tapered profile disrupts the shear force that would otherwise occur in removing the release liner from the dressing and minimizes damage to the dressing (e.g., separation of the adhesive hydrogel from the backing layer) during use.

In one embodiment, an island dressing is provided, comprising a backing that comprises a first major surface; an adhesive located on the first major surface of the backing; a hydrogel island pad proximate the first major surface of the backing, wherein the hydrogel comprises less than 45% water; and a release liner; wherein at least a portion of the perimeter of the hydrogel pad is tapered proximate the area that the hydrogel pad and release liner separate during liner removal.

In another embodiment, an island dressing is provided, comprising a backing that comprises a first major surface; an adhesive located on the first major surface of the backing; a hydrogel island pad proximate the first major surface of the backing; and a release liner; wherein at least a portion of the perimeter of the hydrogel pad is tapered proximate the area that the hydrogel pad and release liner separate during liner removal; and wherein the average maximum peel force to initiate separation of an one-inch wide untapered hydrogel pad and a release liner is at least 25% greater than the average maximum peel force of the tapered hydrogel pad and the release liner, when measured by the T-peel Test Method performed after conditioning the island dressing for one week at 50 degrees C.

In another embodiment, an island dressing is provided, comprising a backing that comprises a first major surface; an adhesive located on the first major surface of the backing; an adhesive hydrogel island pad proximate the first major surface of the backing; and a release liner; wherein at least a portion of the perimeter of the hydrogel pad is tapered proximate the area that the hydrogel pad and release liner separate during liner removal.

As used herein "hydrogel," and "hydrophilic gel" refers to a continuous phase of a hydrophilic polymer that is capable of swelling on contact with water and other hydrophilic swelling agents. The term is used regardless of the state of hydration. Useful hydrogels will absorb at least 40% by weight based on the hydrogel's weight in an anhydrous state. Hydrogels are hydrophilic polymers characterized by their hydrophilicity (i.e., capable of absorbing large amounts of fluid such as wound exudate). The hydrogels are typically transparent or translucent, regardless of their degree of hydration. Hydrogels are generally distinguishable from hydrocolloids, which typically comprise a hydrophobic matrix that contains dispersed hydrophilic particles.

The terms "beveled," "contoured," "stepped," and "tapered" are used interchangeably to refer to a progressively thinning profile of at least a portion of the perimeter of the hydrogel pad where separation of the liner peel from the hydrogel pad is initiated.

These and various other advantages and features characterizing the invention are pointed out with particularity in the claims annexed hereto and forming a part hereof. However, for a better understanding of the invention, its advantages, and objects obtained by its use, reference should be made to the accompanying drawings and descriptive matter, in which embodiments of the invention are illustrated and described.

BRIEF DESCRIPTION OF THE DRAWINGS

The invention will be further described with reference to the drawings, wherein corresponding reference characters indicate corresponding parts throughout the several views, and wherein.

Figure 1:
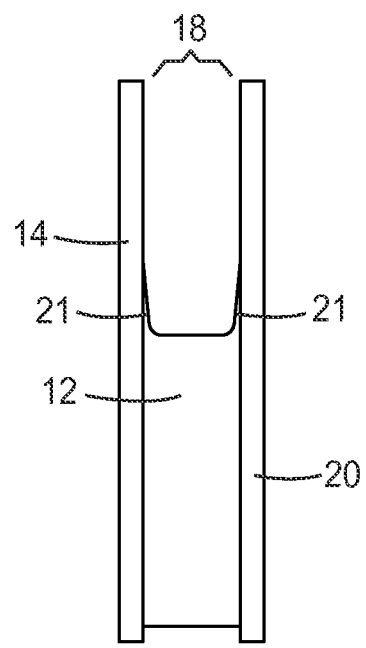
FIG. 1 is an exemplary enlarged side cross-sectional view of the adhesive hydrogel after shrinkage.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is directed to an adhesive hydrogel dressing as well as to methods of applying the dressing to a patient. The dressing generally comprises an adhesive hydrogel pad, a backing layer, and an adhesive layer on the backing layer facing the hydrogel pad. The adhesive layer and backing layer form a perimeter around the hydrogel pad and hold the hydrogel pad in place on a surface. The perimeter formed by the adhesive layer and backing layer keeps the hydrogel pad properly positioned, and also helps maintain a sterile environment around the application surface.

The adhesive layer and backing layer are typically extremely thin, and generally very flexible. If the adhesive layer and backing layer are not properly supported during application they can easily fold over and adhere to themselves, preventing proper application over a surface. The adhesive layer and backing layer are optionally supported by a removable carrier attached to the top face of the backing layer. A release liner is provided to contact the adhesive and the adhesive hydrogel pad. Both the liner and conformable backing layer coated with the adhesive extend beyond the edges of the hydrogel pad.

The adhesive hydrogel composition is formed with at least a portion of the hydrogel pad's perimeter having a beveled, contoured, stepped or tapered edge. Tapering or beveling at least a portion of the hydrogel pad's perimeter overcomes the problems with poor or inconsistent liner release that can occur with low modulus highly conformable hydrogel compositions, such as those described herein. While not being bound by theory, the hydrogel compositions, after aging under low humidity conditions, can exhibit liner lock-up. Liner lock-up is generally considered the inability to remove the release liner without damaging or irreversibly distorting the dressing, which can result in dressing application failures.

Liner lock-up of the hydrogel pad on the release liner can occur for at least two reasons. First, the hydrogel composition, upon exposure to aging conditions (e.g., at least one week at less than 50% relative humidity at room temperature) will lose volatile components, such as water. The loss of volatile components results in shrinkage of the hydrogel composition, thereby generating a concave meniscus of the hydrogel bridging the backing layer and release liner, as shown in FIG. 1

Second, the hydrogel composition typically has residual elasticity with an elastic recovery or shrinkage. In some embodiments, the hydrogel compositions comprise internal stress forces that have built through processing of the hydrogel compostions to form for example, a pad construction of the hydrogel. After processing, these internal stresses cause the hydrogel compositions to experience shrinkage as the internal stresses act as a force causing elastic recovery of the hydrogel.

The effect of both moisture removal and internal stresses can separately, or in combination, affect meniscus formation. The volume movement or shrinkage of the hydrogel composition may be governed similarly to laminar flow of a viscous fluid under Poiseuille's law. Poiseuille's law is the physical law concerning the voluminal laminar stationary flow F of an incompressible uniform viscous liquid (i.e., a Newtonian fluid) through a cylindrical tube with constant circular cross-section.

Per Poiseuille's law, the volume movement is related to the radius of the tube the fluid is flowing to the fourth power. The elastic recovery of the hydrogel composition may behave similarly, considering the elastic recovery forces to follow the same relation as a pressure differential in Poiseuille's law. As the thickness of the hydrogel pad increases, the concave meniscus generated increases, affecting volume flow. Similarly, a significant reduction in volume flow, and hence meniscus formation, due to elastic recovery is decreased as the thickness of the hydrogel decreases.

The adhesive hydrogel compositions are typically coated to form hydrogel pad with thicknesses in excess of 30 mils, and more preferably in excess of 40 mils, and even more preferably in excess of 50 mils. By beveling or tapering at least a portion of the perimeter of the adhesive hydrogel pad to a tapered profile at the point where liner peel is initiated results in substantially reduced peel forces upon initiation of release liner removal.

Typically, hydrogels suitable for use in the dressings described herein comprise less than 45% water, more preferably less than 30% by weight water, and most preferably less than 20% by weight water, based on the total weight of the hydrogel composition.

For example, the adhesive hydrogel composition can comprise a hydrogel comprising about 10% water at 50% relative humidity (RH) and 22° C. and about 6% water at 36% RH and 22° C. Under about 0% RH and 22° C. aging conditions, the moisture or water content of the hydrogel can drop below 3% by wt. At these moisture levels, the hydrogel modulus increases and the hydrogel's peel adhesion increases in relation to typical release liners. This increase in modulus and peel adhesion, when combined with hydrogels of significant thickness (such as thicknesses greater than 40 mils, preferably greater than 60 mils), will cause the release liner to traverse from peel removal to a shear removal, thereby dramatically altering (increasing) the force necessary to remove the liner.

The determination of the likeliness of a hydrogel composition to form this meniscus bridging the liner and backing can be assessed by a relatively simple method. With a hydrogel composition between two release liners, one on each side, several samples can be cut in the downweb and crossweb directions precisely using a cutting die, for example, a 3.8 cm by 5.1 cm die. The sample can be gently removed from the two liners and attached to a surface, preferably a shelf, along one of the narrower 3.8 cm dimension of the hydrogel. Approx 0.5 cm can contact the surface, leaving the remaining 4.5 cm to dangle downward, untouched by any surface. After 24 hours, the sample can be measured for width at the lowest point.

If the width remains unchanged, (i.e. the width is 3.8 cm) the sample has experienced 0% shrinkage. Correspondingly, if the hydrogel is now 1.9 cm wide, it has experienced 50% shrinkage. The samples can also be preweighed and post weighed to determine if they have gained or lost water or other volatiles. A sample which has not changed weight but has experienced shrinkage is likely due to residual elastic recovery forces within the hydrogel. The conditions can also be varied with respect to humidity and temperature to effect meniscal formation of the hydrogel.

Hydrogels as described herein typically experience shrinkage levels of at least 10%, and more often 40% depending on hydrogel processing, the calendaring gap used in manufacturing, and moisture levels. Typically higher moisture levels in the hydrogel result in low elastic recovery shrinkage but higher volatile shrinkage under low humidity conditions. Since process conditions can be difficult to achieve that minimize both shrinkage forces, the tapered profile hydrogel provides a solution to address potential liner lock-up using these compositions.

Figure 2:
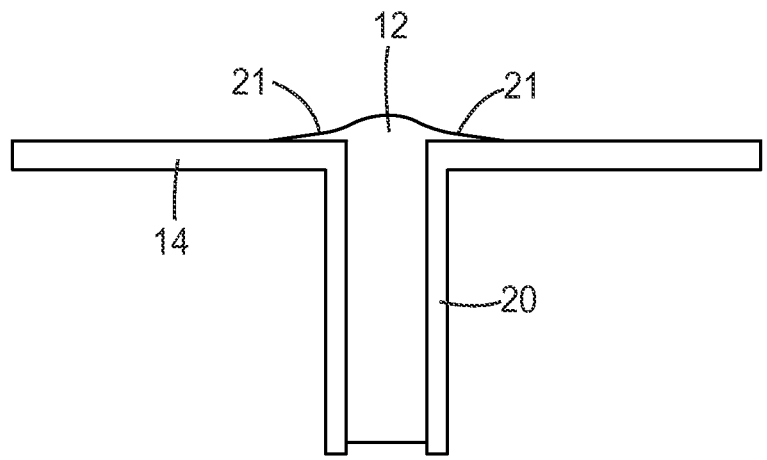
FIG. 2 is an exemplary enlarged side cross-sectional view of the adhesive hydrogel during peel.

FIGS. 1 and 2 schematically illustrate the difference in hydrogel characteristics in a hydrogel composition that lacks a tapered portion on the perimeter. FIG. 1 depicts a hydrogel pad 12 between release liner 20 and backing layer 14 (coated with an adhesive) after contraction of the hydrogel in the center as the hydrogel pad 12 is exposed to aging conditions. The hydrogel pad 12 forms a meniscus 18 with extensions 21 of the hydrogel pad 12 along the surface of both the release liner 20 and the backing layer 14 (coated with an adhesive). The extensions 21 facilitate the hydrogel pad 12 going into a shear mode as the release liner 20 and backing layer 14 are pulled apart from each other in a T-peel fashion as depicted in FIG. 2.

Figure 3:
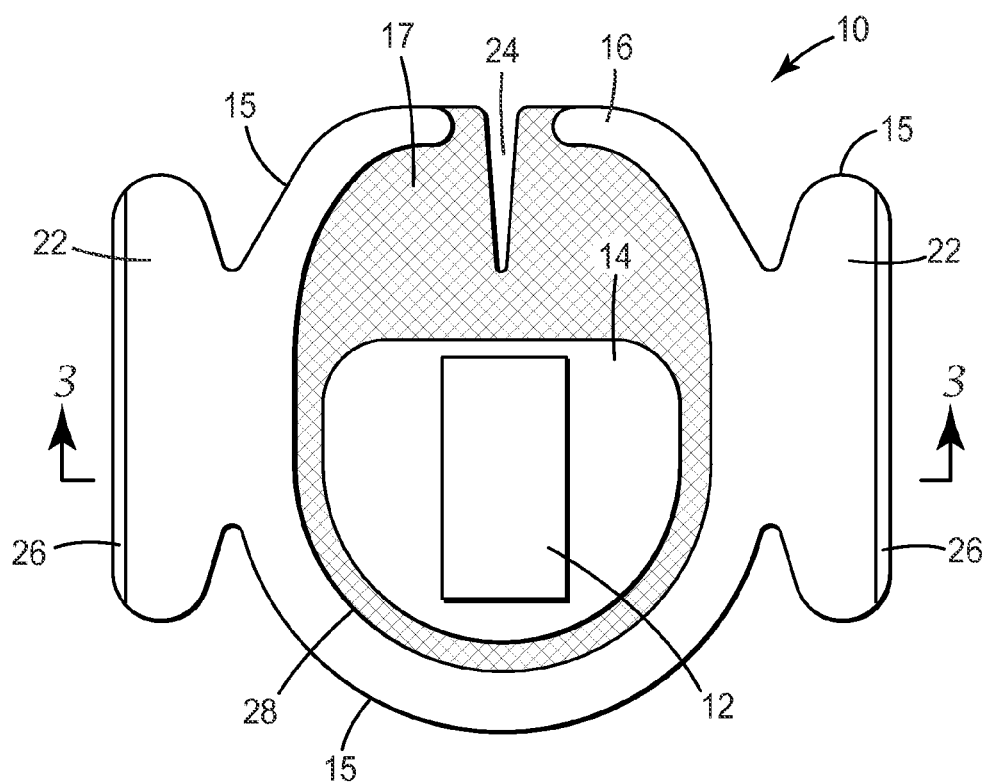
FIG. 3 is a top plan view of a hydrogel dressing configured and arranged in accordance with an implementation of the invention.
Figure 4:
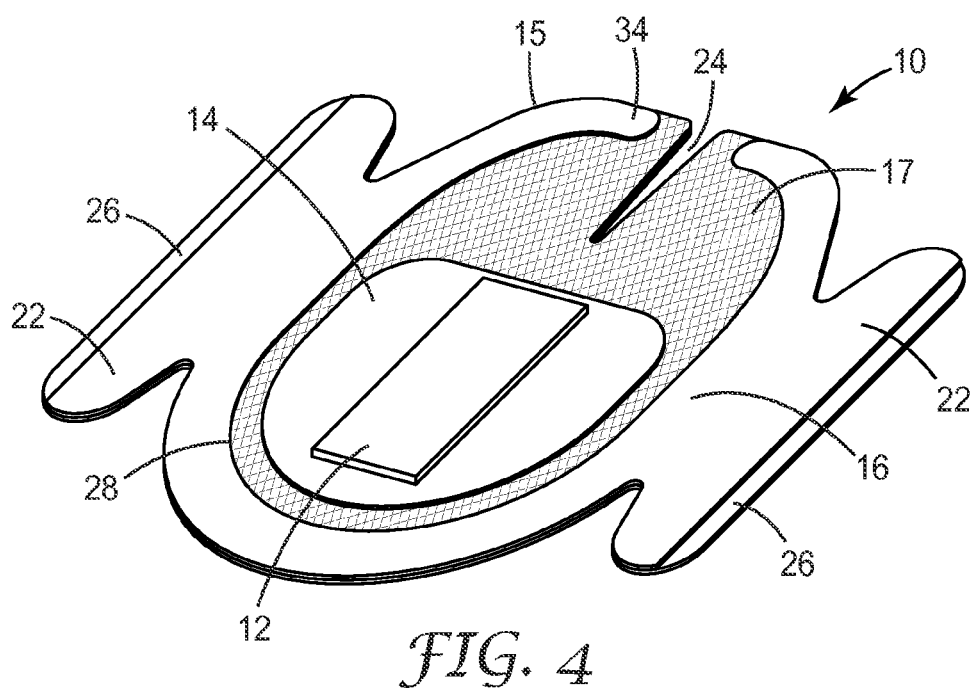
FIG. 4 is a top perspective view of the hydrogel dressing of FIG. 3.
Figure 5:
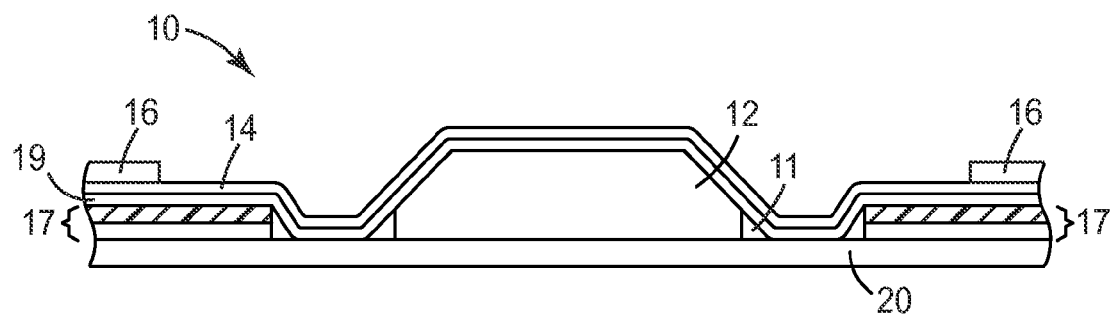
FIG. 5 is a side schematic view of the dressing of FIGS. 3 and 4 taken substantially along line 3-3 of FIG. 3.

FIGS. 3-5 depict a preferred embodiment of the hydrogel pad dressing and delivery system designated in its entirety by the reference numeral 10. FIG. 5 is a cross section of a dressing 10, taken along lines 3-3 of FIG. 3. The dressing 10 includes a hydrogel pad 12 located proximate the center of the dressing 10. Although hydrogel pad 12 is shown as proximate the center of dressing 10 and as having a rectangular shape, it can take any appropriate shape and/or can be located off-center on the dressing 10 as desired. Hydrogel pad 12 typically contains an antimicrobial agent, described further below. The hydrogel pad 12 is covered by an adhesive layer on a backing layer 14 that extends out to the perimeter 15 of the dressing 10. The backing layer 14 is typically extremely thin, flexible, and either transparent or translucent, allowing the hydrogel pad 12 to be viewed through it.

In FIGS. 3-5, an optional adhesive laminate 17 (as viewed through transparent backing layer 14) is also provided. One type of adhesive laminate is described in U.S. Pat. No. 5,088,483. The adhesive laminate 17 can be a laminate of an adhesive and a substrate such as a film or fabric.

As shown in FIG. 5, adhesive laminate 17 is affixed to the backing layer 14 after the bottom face of the backing layer 14 is coated with a pressure sensitive adhesive, with the adhesive laminate 17 exposed so that the adhesive laminate 17 will adhere to the skin or other surface to which the dressing 10 is applied. The adhesive laminate 17 may be provided on the backing layer 14 in any pattern.

Adhesive laminate 17 is applied to at least a portion of backing layer 14 on the same side of backing layer 14 as the adhesive layer 19 (as shown in FIG. 5). A release liner 20 covers the adhesive layer 19, the hydrogel pad 12, and the adhesive laminate 17. Release liner 20 is optionally die cut or may optionally extend beyond the adhesive coated face of backing layer 14 to enable easy removal by the user.

The adhesive laminate 17 may provide some reinforcing and conformability properties to the backing material. This adhesive reinforcement may be a film/adhesive laminate, such as HYTREL (DuPont, Wilmington, Del.) film and tackified acrylate adhesive such as a copolymer of iso-octyl acrylate, acrylic acid and FORAL 85 (a triglyceryl ester of reduced abietic acid, commercially available from Hercules Chemical Co., Wilmington, Del.) tackifier. Another adhesive laminate 17 may be a fabric/adhesive laminate. Examples of nonwoven fabric/adhesive laminates include embodiments such as disclosed in U.S. Pat. No. 4,366,814 and available commercially as STERI-STRIP," (3M, St. Paul, Minn.) elastic skin closure, a nonwoven elastomeric melt blown web of thermoplastic elastomeric small diameter fibers, or CEREX (Monsanto, St. Louis, Miss.) spun bonded nylon and adhesive. Woven fabric/adhesive laminates include embodiments such as cotton cloth laminated to a rubber based adhesive.

A carrier layer 16 is optionally positioned over the backing layer 14. The carrier layer 16 can be a single piece of material, such as a polymeric film, or can be two or more distinct pieces. In the embodiment of FIGS. 3-5, the carrier layer 16 comprises at least one portion that extends beyond the edge of the backing layer 14 of the dressing 10 to form a tab 22. The tab 22 can be held during positioning of the dressing 10.

The carrier layer 16 extends along substantially the entire periphery of the backing layer 14 and forms a window 28 exposing a portion of the backing layer 14 overlying the hydrogel pad 12 with the backing layer 14 sandwiched between the carrier layer 16 and hydrogel pad 12. As used herein, the term "sandwiched" means that one layer is intermediate or between two other layers. For example, the backing layer 14 may be considered an intermediate layer between the carrier layer 16 and the hydrogel pad 12, and thus is "sandwiched" between the carrier layer 16 and hydrogel pad 12.

A window 28 may be cut (e.g., controlled depth die cut) from a carrier blank to form a carrier layer 16 having a window exposing a portion of the top surface of the backing layer 14. The cut or window portion of the carrier blank may be either removed during manufacturing or by the consumer. Removal during manufacturing eliminates one step in the delivery process for previously known window style dressings and reduces the waste stream at the consumer level. Some customers, however, prefer that the portion of the carrier covering window 28 remains intact until the dressing 10 reaches the consumer.

In the embodiment shown in FIGS. 3-5, the carrier layer 16 has an opening such that the frame extends slightly less than completely around the perimeter of the backing layer 14. The opening would allow the dressing to be placed over catheters or other devices while still attached to the frame to increase the ease of handling of backing layer 14.

In preferred embodiments, a notch 24 may be provided in dressing 10. In applications using the dressings with other devices, such as a percutaneous device, the notch 24 allows the dressing 10 to conform around bulky parts of the other device, or may conform around portions of the device that exit the area of dressing application, such as a catheter line.

Referring again to FIGS. 3-5, the dressing 10 typically includes a release liner 20, also having a tab 26. The release liner 20 covers the surface of the dressing 10 applied to the patient, generally making contact with the hydrogel pad 12, the periphery of the adhesive laminate 17, and the adhesive 19. The release liner 20 typically remains attached to dressing 10 until a user is ready to apply the dressing. The release liner 20 may be a single piece or multiple piece release liner, and may be part of or laminated to the package (not shown) containing the dressing, or merely enclosed along with the dressing within the package.

Pressure sensitive adhesive layer 19 is generally provided on one major surface of the backing layer 14 in order to make it adhesive, and a low adhesion coating (low adhesion backsize or LAB) is provided on the other major surface of the backing layer 14 on the side that comes in contact with the carrier layer 16. The low adhesion coating reduces the need to change the dressing 10 due to unwanted dressing removal when other tapes or devices are placed on the dressing 10 and removed, and reduces the surface friction of the dressing 10 on linen or other fabrics, thereby offering additional protection against the accidental removal of dressing 10. A description of a low adhesion backing material suitable for use with the present invention can be found in U.S. Pat. Nos. 5,531,855 and 6,264,976, which are compatible with a heat seal bond described below, and are incorporated herein in their entirety.

The hydrogel pad 12 of dressing 10 is sometimes referred to as an "island pad" because the backing layer 14 extends substantially beyond the hydrogel pad 12, typically beyond the entire periphery of the hydrogel pad 12. As used herein, an island pad also includes constructions wherein the backing layer extends partially beyond the hydrogel pad 12, for example, at least 50% of the periphery of the hydrogel pad 12. For example, the length and width of the hydrogel pad can be 3 cm by 7 cm, while a backing for this pad can be 10 cm by 15.5 cm.

The carrier layer 16 is preferably attached to the second major surface of the backing layer 14 (over the low adhesion backing). The bond between the carrier layer 16 and the backing layer 14 is stronger than the bond between the adhesive layer 19, adhesive laminate 17, or hydrogel pad 12, and the release liner 20 so that the backing layer 14 remains attached to the carrier layer 16 when the release liner 20 is removed from the dressing 10. Once the release liner 20 and dressing 10 are separated, only the carrier layer 16 and hydrogel pad 12 provide significant rigidity to the backing layer 14.

Various other embodiments are contemplated from the aspects shown in FIGS. 3-5. For example, the backing layer 14 can be multiple films or coatings without diverging from the invention or deviating from the meaning of the term "film" as used herein. Similarly, the hydrogel pad 12 can include multiple sub-layers, including films, webs, sheets, etc. Also, additional layers and films of other materials can be added between the materials described herein.

The hydrogel pad 12 can comprise a hydrogel composition as described further below thickness of at least 40 mils, more preferably 50 mils, and most preferably 60 mils. The backing layer 14 can comprise a transparent elastic polymeric film (e.g., urethane) having a thickness in the range of 0.02 to 0.2 mm and most preferably 0.021-0.051 mm. As shown in FIG. 5, the thickness of the hydrogel pad 12 relative to the other layers of the dressing 10 can create an air gap 11 around the periphery of the hydrogel pad 12.

Figures 6A, 6B, 6C:
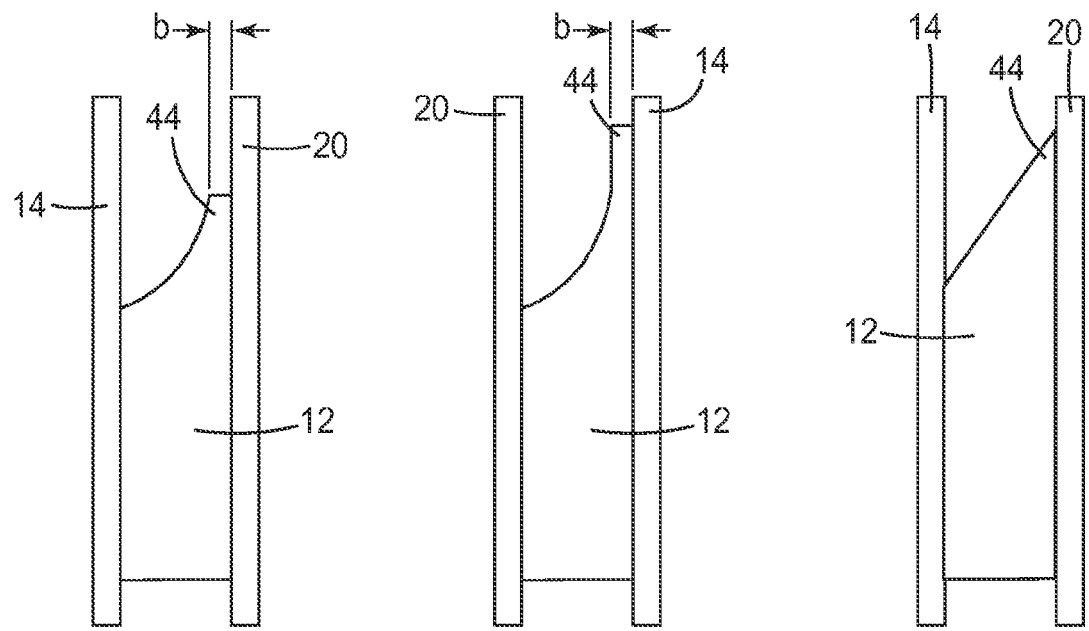
FIGS. 6a-6c is an enlarged side cross-sectional view of exemplary embodiments with tapered or beveled edges.

As shown in FIGS. 6a-c, the hydrogel pad 12 can be tapered in a variety of geometries that result in a tapered profile 44 (relative to the thickness of the majority of the hydrogel pad 12) along at least a portion of the perimeter of the hydrogel pad 12 at the interface or point where liner peel is initiated. The tapered profile 44 can be formed against either the backing layer 14 (as shown in FIG. 6b) or the release liner 20 (as shown in FIG. 6a) during manufacture, so long as the geometry and thickness of the tapered profile 44 minimizes or otherwise affects the formation or legs of a meniscus 18 with extensions 21 as shown in FIGS. 1-2. It should be noted that the FIGS. 6a, b and c do not attempt to describe the exact intimacy of the liner to the dressing at the tapered hydrogel edge. For purposes of depicting the possible geometries of the tapered profile 44, the backing layer 14 and release liner 20 have been shown as separated. FIG. 5 is a more accurate depiction of an exemplary embodiment with contact between backing 14 (coated with adhesive layer 19), hydrogel pad 12, and release liner 20 when assembled.

The tapered profile 44 is preferably less than 40 mils at the liner peel interface. As shown in FIGS. 6a-c liner peel interface has a thickness dimension b. The thickness dimension b at liner peel interface is preferably less than 40 mils, more preferably less than 30 mils, and even more preferably less than 20 mils.

The tapered profile 44 at the liner peel interface minimizes the peel force necessary to initiate peel of the hydrogel pad 12 from the release liner 20 or prevents liner removal difficulty. Difficulty in peel removal of the liner from the hydrogel pad 12 can encompass both liner lock-up, (the inability to remove the liner without damaging or irreversibly distorting the dressing) and reduced ease in removing the liner where the average maximum peel force of an untapered hydrogel pad is increased greater than 25% relative to the same construction of a hydrogel pad 12 with a tapered profile 44, and measured during liner removal by the T-peel test described below.

Due the to the visco-elastic nature of the hydrogel composition as described herein, the tapered profile of the hydrogel will experience shrinkage, and affect the degree of taper imparted during manufacture. Despite this contraction of the tapered profile, the tapered profile should remain thin enough (e.g., less than 40 mils) to achieve the reduced peel forces necessary to separate the hydrogel pad from the release liner during the liner's removal.

Figure 7A:
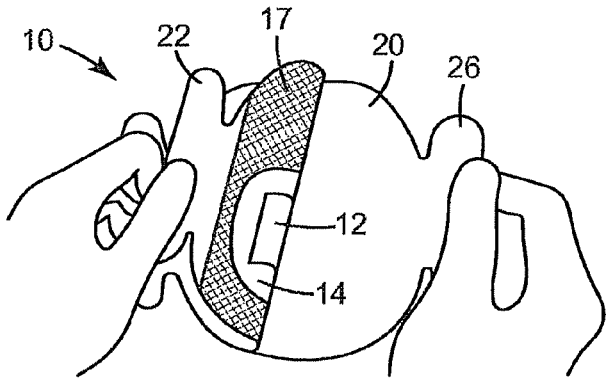
FIGS. 7a-7d is an exemplary depiction of a method of applying the dressing of FIG. 3-5 to a patient.
Figure 7B:
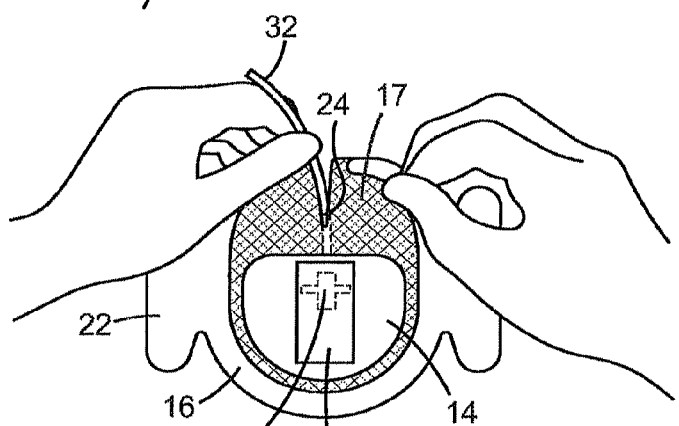

FIGS. 7a-d depict an exemplary embodiment applying the dressing 10 of FIGS. 3-5 to a patient. In FIGS. 7a-d, the hydrogel dressing 10 is depicted as a dressing covering a percutaneous device, such as an intraveneous catheter (IV). The dressing 10 is typically applied to a patient by first cleaning the application area and inserting the IV. The release liner 20 is then removed from the dressing, exposing the bottom of the hydrogel pad 12, the adhesive laminate 17 and the backing layer 14 (coated with adhesive layer 19), as shown in FIG. 7a. Once removed from release liner 20, hydrogel pad 12 is brought in contact with the catheter site, covering catheter device 30, and then the edges of the dressing 10 are gently and smoothly pressed against the patient, thereby bringing the exposed adhesive perimeter of the backing layer 14 and the adhesive laminate 17 in contact with the patient, as shown in FIG. 7b. The catheter line 32 exits the dressing 10 at the notch 24. This configuration aids in placement of hydrogel pad 12 to optimize secural of the lumen and hub of a catheter.

Figure 7C:
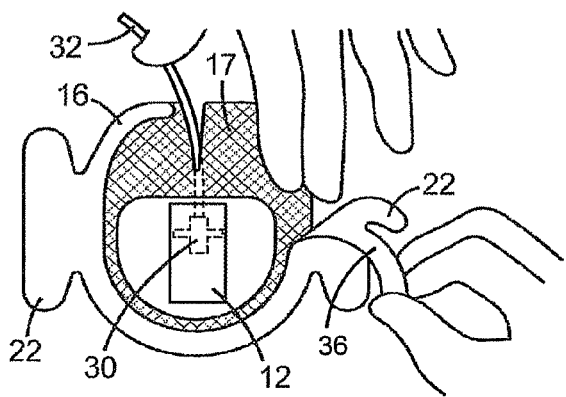
Figure 7D:
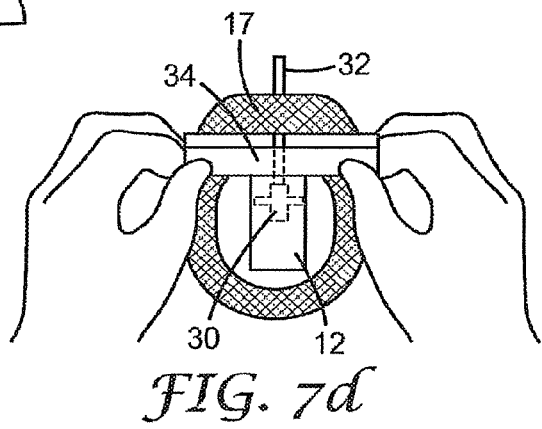

After the dressing 10 is properly in position and adhered to a patient's skin, the carrier layer 16 can be removed, as shown in FIG. 7c. Generally removal of carrier layer 16 is accomplished by grasping the carrier layer at area 36 and using a peeling motion toward the edges of the dressing 10 to remove the carrier layer 16. After application of the dressing 10, optional tapes 34 may be placed over the dressing 10 to cover catheter line 32 exiting dressing 10 at notch 24. The tapes 34 may be provided with the dressing 10 or may be supplied separately.

The layers and materials discussed above are further described in detail below.

Hydrogel Materials

Suitable hydrogel compositions include, for example, a natural hydrogel, such as pectin, gelatin, or carboxymethylcellulose (CMC) (Aqualon Corp., Wilmington, Del.), a semi-synthetic hydrogel, such as cross-linked carboxymethylcellulose (X4ink CMC) (e.g. Ac-Di-Sol; FMC Corp., Philadelphia, Pa.), a synthetic hydrogel, such as cross-linked polyacrylic acid (PAA) (e.g., CARBOPOL™ No. 974P; B.F. Goodrich, Brecksville, Ohio), or a combination thereof.

In most embodiments, the hydrogel dressing comprises a swellable, crosslinked poly(N-vinyl lactam), a swelling agent and a modifying polymer present in an amount sufficient to form a cohesive, pressure-sensitive adhesive composition as described further in Applicants pending application, U.S. Ser. No. PCT/IL06/00708. The amount of swelling agent to be mixed with the crosslinked swellable poly(N-vinyl lactam) can range from about 50 to about 90 weight percent of the composition. Consequently, exclusive of any biocompatible and/or therapeutic and/or ionically-conductive materials to be added to the composition, the weight percent of the swellable poly(N-vinyl lactam) can be from about 10 to about 50 weight percent. When the poly(N-vinyl lactam) is poly(N-vinyl pyrrolidone), the weight percent of poly(N-vinyl pyrrolidone) can range from about 15 to about 45 percent. In particular embodiments, the poly (N-vinyl pyrrolidone) can range from about 18 percent to about 35 percent.

In most embodiments, the adhesive composition of the present invention comprises a swellable, poly(N-vinyl lactam) that is radiation-crosslinked, typically while the lactam is in a solid form. In other embodiments, the poly (N-vinyl) lactam is crosslinked by free-radical polymerization, either in bulk or in solution, of a precursor containing an N-vinyl lactam monomer, optionally other monomers, and a crosslinking compound as described in U.S. Pat. No. 4,931,282. Poly(N-vinyl lactam) useful in the present invention can be provided in any form susceptible to being crosslinked such as the solid forms described in U.S. Pat. Nos., 4,931,282, 5,225,473 and 5,389,376. Typically, the poly(N-vinyl lactam) is a homopolymer of N-vinyl-2-pyrrolidone.

After exposure to ionizing radiation, poly(N-vinyl lactam) can have a Swelling Capacity in water of at least about 15, typically at least about 30, and often at least about 40 as described in U.S. Pat. No. 5,409,966, which is incorporated herein by reference. Poly(N-vinyl lactam) in any solid form may be crosslinked for use when subjected to ionizing radiation from a high-energy source.

The modifying polymer is present in the adhesive composition to maintain and/or increase cohesiveness while reducing adhesiveness. When added with the swelling agent, the modifying polymer becomes solubilized or suspended in the swelling agent. Typically, the modifying polymer will form a viscous solution or viscous gel when combined with the swelling agent in a ratio of modifying polymer to swelling agent of 1:9.

The choice of swelling agent typically will determine the appropriate modifying polymer to accomplish a reduction in adhesion while maintaining or improving cohesion of the adhesive composition. Modifying polymers that are poorly solubilized in one swelling agent may be highly swollen in a different swelling agent for use in the present invention. In some embodiments, examples of suitable modifying swellable polymers include, but are not limited to, polysaccharides, polysaccharide derivatives, acrylates, acrylate derivates, cellulose, cellulose derivatives, and combinations thereof.

In particular embodiments, modifying swellable polymers for use in the present invention are hydroxypropyl guar; guar gum; hydroxyethyl cellulose; hydroxypropyl cellulose; hydroxypropyl methylcellulose; polymeric quaternary ammonium salt of hydroxyethyl cellulose reacted with trialkyl ammonium substituted epoxide; copolymers of hydroxyethyl cellulose and diallyldimethyl ammonium chloride; and derivatives and combinations of the foregoing.

The amount of modifying polymer can range up to about 50 weight percent of the composition. Consequently, exclusive of any biocompatible and/or therapeutic and/or ionically-conductive materials to be added to the composition, the weight percent of the modifying polymer can be from about 0.1 to about 40 weight percent. When the modifying polymer is hydroxypropyl guar, the weight percent of hydroxypropyl guar can range from about 1 to about 20 percent.

The hydrogel composition also comprises a swelling agent which can swell both the crosslinked poly(N-vinyl lactam) polymer and the modifying polymer, and which is biocompatible with human skin. Nonlimiting examples of swelling agents useful to swell the poly(N-vinyl lactam) include monohydric alcohols (e.g., ethanol and isopropanol), polyhydric alcohols, (e.g., ethylene glycol, propylene glycol, polyethylene glycol (Molecular Weight between 200 and 600) and glycerin), ether alcohols (e.g., glycol ethers), other polyol swelling agents which do not cause skin irritation or toxic reaction, and water.

Depending on the ultimate use desired for the adhesive composition, non-volatile and/or volatile swelling agents may be used. One suitable swelling agent may comprise volatile swelling agent and non-volatile swelling agent, such as a mixture of glycerin or polyethylene glycol with water. In some embodiments, non-volatile swelling agents may be used by themselves such as, for example, glycerin or polyethylene glycol. Likewise, volatile swelling agents such as water may be used by themselves in the compositions of the invention. For this invention, "essentially non-volatile" means that a swelling agent as used in the present invention will render the adhesive polymer, such as radiated poly(N-vinyl lactam), sufficiently cohesive and pressure sensitive adhesive, such that less than ten percent (10%) of a given volume of nonvolatile swelling agent evaporates after exposure to processing or storage conditions.

The swelling agent can be added in an amount ranging from about 50 to about 90 weight percent of the adhesive composition and preferably from about 60 to about 80 weight percent. In some embodiments, glycerin and polyethylene glycol are chosen to be the essentially non-volatile swelling agent. Both glycerin and polyethylene glycol can comprise up to 100 weight percent of the swelling agent.

Hydrogel pad 12 is useful for containing a number of substances, optionally including antimicrobial agents, drugs for transdermal drug delivery, chemical indicators to monitor hormones or other substances in a patient, etc.

Antimicrobial Agents

The hydrogel composition can deliver an antimicrobial agent to the skin, reducing the likeliness of an infection to a percutaneous device or to treat infections of the skin or wounds. In most embodiments, the antimicrobial agent is added in levels up to 10% by weight of the total composition.

There are numerous biologically active materials, which include antimicrobial agents. Examples of antimicrobial agents include parachlorometaxylenol; triclosan; chlorhexidine and its salts such as chlorhexidine gluconate, poly hexamethylene biguanide and its salts such as poly hexamethylene biguanidine chloride, iodine, idodophors; fatty acid monoesters; poly-n-vinyl pyrrolidone-iodophors; silver oxide, silver and its salts, peroxides (e.g. hydrogen peroxide), antibiotics (e.g. neomycin, bacitracin, and polymixin B). Other suitable antimicrobial agents are those listed in U.S. patent Ser. No. 10/456,811, filed Jun. 5, 2003.

A method of preparing a pressure-sensitive adhesive composition of the present invention comprises mixing crosslinked poly(N-vinyl lactam) with a swelling agent and a modifying polymer, and other additives in a solvent which is may be somewhat volatile at or above ambient temperatures. Typically, the swelling agent, modifying polymer, and other additives, such as antimicrobial agents, are in essentially unirradiated form. Examples of suitable volatile solvents include water, ethanol, methanol, and isopropanol. A quantity of the resulting suspension is then cast onto a surface of a substrate, such as a release liner or a backing material and then stored. The volatile solvent is evaporated by heating such as by the application of microwave energy, infrared energy, or by convective air flow or the like, in order to form a cohesive, pressure-sensitive adhesive composition on the substrate. Often, a drying oven heated to about 65 degree C. may be employed for the evaporation step. A product release liner can optionally be laminated over the exposed surface of the composition to protect it from contamination.

Backing Materials

Suitable backing materials for backing layer 14 include, for example, nonwoven fibrous webs, woven fibrous webs, knits, films and other familiar backing materials. The backing materials are typically translucent or transparent polymeric elastic films. The backing can be a high moisture vapor permeable film backing. U.S. Pat. No. 3,645,835 describes methods of making such films and methods for testing their permeability.

The backing advantageously should transmit moisture vapor at a rate equal to or greater than human skin. In some embodiments, the adhesive coated backing layer transmits moisture vapor at a rate of at least 300 g/m$^2$/24 hrs/37° C./100-10% RH, frequently at least 700 g/m$^2$/24 hrs/37° C./100-10% RH, and most typically at least 2000 g/m$^2$/24 hrs/37° C./100-10% RH using the inverted cup method.

The backing layer 14 is generally conformable to anatomical surfaces. As such, when the backing layer 14 is applied to an anatomical surface, it conforms to the surface even when the surface is moved. The backing layer 14 is also conformable to animal anatomical joints. When the joint is flexed and then returned to its unflexed position, the backing layer 14 can be made such that it stretches to accommodate the flexion of the joint, but is resilient enough to continue to conform to the joint when the joint is returned to its unflexed condition.

A description of this characteristic of backing layers 14 for use with the present invention can be found in issued U.S. Pat. Nos. 5,088,483 and 5,160,315. Specific suitable backing materials are elastomeric polyurethane, co-polyester, or polyether block amide films. These films combine the desirable properties of resiliency, high moisture vapor permeability, and transparency found in backings.

Carrier Layer

The material used to form the carrier layer 16 is generally substantially more rigid than the backing layer 14 to prevent the backing layer 14 from improperly wrinkling during application to a patient. The carrier layer 16 can be heat-sealable to the backing layer 14 with or without a low adhesion coating described above. In general, the carrier layer materials can include, but are not limited to, polyethylene/vinyl acetate copolymer-coated papers and polyester films. One example of a suitable carrier layer material is a polyethylene/vinyl acetate copolymer coated super calendared Kraft paper (1-80BKG-157 PE; LOPAREX of Willowbrook, Ill.).

The carrier layer 16 can include perforations to aid in separating portions of the carrier layer 16 after application of the dressing 10 in a patient. Spacing and shape of the perforations are adjusted to give a carrier layer with relatively easy to tear performance on removal of the carrier layer from the applied dressing. The perforations may be shaped in accordance with any of the accepted perforation patterns including linear, angled, Y-shaped, V-shaped, dual-angled offset, sinusoidal, etc.

Adhesive Layer

Various pressure sensitive adhesives can be used to form adhesive layer 19 on the backing layer 14 to make it adhesive. The pressure sensitive adhesive is usually reasonably skin compatible and "hypoallergenic", such as the acrylate copolymers described in U.S. Pat. No. RE 24,906. Particularly useful is a 97:3 iso-octyl acrylate: acrylamide copolymer, as is 70:15:15 isooctyl acrylate: ethyleneoxide acrylate: acrylic acid terpolymer described in U.S. Pat. No. 4,737,410, is suitable. Additional useful adhesives are described in U.S. Pat. Nos. 3,389,827, 4,112,213, 4,310,509, and 4,323,557. Inclusion of medicaments or antimicrobial agents in the adhesive is also contemplated, as described in U.S. Pat. Nos. 4,310,509 and 4,323,557.

The adhesive layer 19 can be coated on the backing layer 14 by a variety of processes, including, direct coating, lamination, and hot lamination.

Release Liner

Release liner 20 suitable for use as described herein can be made of kraft papers, polyethylene, polypropylene, polyester or composites of any of these materials. The films are preferably coated with release agents such as fluorochemicals or silicones. For example, U.S. Pat. No. 4,472,480 describes low surface energy perfluorochemical liners. The liners are papers, polyolefin films, or polyester films coated with silicone release materials. Examples of commercially available silicone coated release papers are POLYSLIK™, silicone release papers available from Rexam Release (Bedford Park, Ill.) and silicone release papers supplied by LOPAREX (Willowbrook, Ill.). Other non-limiting examples of such release liners commercially available include siliconized polyethylene terephthalate films commercially available from H. P. Smith Co. and fluoropolymer coated polyester films commercially available from 3M under the brand "ScotchPak™" release liners.

Methods of Manufacturing

Tapering of the hydrogel can be manufactured by extruding the hydrogel between two process liners, and then sandwiching this multilayer system between the nip of two calender rolls. Profiled portions of the hydrogel can be formed by varying the outer diameter of one of the calender rolls at one or more locations along the length of the calender roll. As familiar to those skilled in the art, changes in diameter of the calender roll create higher pressure and lower pressure nip points produced on the multilayer construction, resulting in the hydrogel layer having different thicknesses across this multilayer system as it exits the calender rolls. The outer diameter of the calender roll can be varied by machining different diameters into the roll or by adding collars (e.g., shims) to the roll at various locations along the length of the roll. One method for adding collars or shims includes wrapping a single width of a thick foam tape around the calender roll at a single location on the calender roll. Multiple locations on the calendar roll may be wrapped to vary the diameter. As familiar to those skilled in the art, further slitting or converting of the hydrogel can be performed after the calendaring step. To manufacture the final product, the tapered portion of the hydrogel can be positioned on the final product dressing such that the tapered portion is proximate the area that the hydrogel pad and release liner separate during liner removal, to ensure adequate liner release.

Other suitable manufacturing methods for tapering a hydrogel pad 12 are described in U.S. Pat. Nos. 4,867,748; 5,131,821; and U.S. Publication No. 2006/0064049 A1.

In one embodiment, the adhesive hydrogel composition is extruded at a thickness of about 50 to 60 mils between release liners on a calendar roll with its outer diameter varied using 1 cm wide bands with 3.5 cm on center. The increased diameter thins the hydrogel pad to about 20 to 40 mils in those locations. Variations in the thickness of the profiled outside the range of 10 to 20 mils may be due to sections of the hydrogel may be thicker due to the visco-elastic nature of the extruded material, as discussed further above.

EXAMPLES

T-Peel Test Method

For each sample the release liner is lightly folded (not creased) just prior to and parallel to the hydrogel edge to facilitate the 180° peel. While holding the sample flat, the product liner is clamped in the top jaw and the remaining layers of the dressing in the bottom jaw. The hydrogel patch is aligned with the lower and upper jaws so that the peel would reach the edge of the hydrogel patch evenly. The sample is left "loose" between the jaws to avoid separating the liner from the hydrogel prior to taking the measurement.

T-Peel measurement is conducted using a Zwick tensile tester, model #288, (available from Zwick USA, Kennesaw, Ga.) or equivalent with the jaw speed set at 6 inches (15.24 cm) per minute and the gauge at 2 inches (5.1 cm). Data is collected for the maximum (peak) peel force in ounce-force units produced during the T-peel. Unless otherwise stated, the standard test liner is a LOPAREX 2 mil (51 micrometer) PET liner with 164Z release coating, available from LOPAREX of Willowbrook, Ill. Unless otherwise stated the standard conditioning for a test sample is drying in an oven at 50° C. for a minimum of 1 week.

Glossary of Components

| Trade Name | Chemical Name | Manufacturer, Address |
|---|---|---|
| GANEX V-216 | Polyvinylpyrrolidone/Hexadecane copolymer | ISP, Wayne, NJ |
| 0.64% EBVP | Crosslinked PVP with 0.64% Ethylene-bis-N-vinyl-2-pyrrolidone (EBVP) crosslinker | 3M/St Paul, MN |
| 1.28% EBVP | Crosslinked PVP with 1.28% EBVP crosslinker | 3M |
| JAGUAR HP-120 | Hydroxypropyl Guar (HPG) | Rhodia, Cranbury, NJ |
| JAGUAR HP-60 | Hydroxypropyl Guar | Rhodia |
| GANEX P904 LC | Butylated poly vinyl pyrrolidone | ISP |
| CHG Solution B.P. | 20% Chlorhexidine Gluconate in Water | Xttrium Labs |
| XPVP | Gamma crosslinked K-90D polyvinylpyrrolidone | ISP Plasdone K-90D PVP processed with 15 Mrad gamma radiation |
| Polyglycerol-3 | Triglycerol | Solvay Interox, Houston, Texas |

Example E1 and Comparative Example C1

The hydrogel adhesive material of Examples E1 and C1 was prepared in the same manner as Example 73 of US patent publication US 20040247655-A1 using amounts of the components shown below, in Table 2.

TABLE 2

| Component | Wt/Wt % |
|---|---|
| Polyglycerol-3 | 61 |
| CHG* | 2 |
| Water** | 9 |
| Crosslinked Polyvinyl Pyrrolidone | 24 |
| Hydroxy propyl Guar | 4 |

*Based on dried weight
**Water content varies with % RH and aging, For example, 50% RH provides 9-10% water by weight.

Comparative Examples C2-C3

Comparative Examples C2-C3 are commercially available hydrocolloid dressings known as COMFEEL, available from Coloplast of Minneapolis, Minn. The COMFEEL product has a tapered section at the edge of the dressing. Example C2 was T-peel measured by starting the peel at the edge of the dressing. Example C3 was prepared by cutting the COMFEEL product at the center of the dressing to create at non-tapered (90°) face to the hydrogel. Example C3 was then T-peel measured by starting the peel at the newly created non-tapered edge.

Dressing Preparation

Hydrogel adhesive Examples E1 and C1 with release liner on both sides were cut to 3 cm by 3 cm. Samples of the tapered edge Example 1 were created by hand cutting with a scissors to form tapered edge with an approximate five degree. Non-tapered samples of the Hydrogel Comparative Example C1 were cut to have a 90 degree edge. Example E1 and Comparative Example C1-C3 were laminated to LOPAREX 2 mil (51 micrometer) PET liner with 164Z release coating, available from LOPAREX of Willowbrook, Ill. A piece of 3M TEGADERM film, available from 3M, St. Paul, Minn., was cut in slight excess of the 3 cm width by 10 cm long and applied over the hydrogel. Contact between the TEGADERM film dressing, the Example hydrogel and the release liner was ensured by light finger pressure applied against the entire length of the construction.

Ten replicate samples were constructed for each Example and Comparative Example configuration. The samples were then placed in an oven at 50° C. for 4 days to dry/evaporate the volatiles. The samples were then placed in a plastic zip lock bag and equilibrated at room temp overnight for a minimum of 10 hrs prior to testing. T-Peel test results for Examples E1 and C1-C3 are shown in Table 3, below.

TABLE 3

| Ex. | Description | Tapered Edge | Ave* Max Peel Force |
|---|---|---|---|
| E1 | Hydrogel CHG Dressing | Yes | 8.90 |
| C1 | Hydrogel CHG Dressing | No | 15.83 |
| C2 | Coloplast COMFEEL | Yes | 7.82 |
| C3 | Coloplast COMFEEL | No | 6.62 |

*Average of 10 samples

Example E2 and Comparative Example C4

Examples E2 and C4 were prepared in the same manner as Example E1, above. Scissors were used to cut the gel at an extremely low angle to produce a low angle slope to the gel for Example E2. Comparative Example C4 was not cut at an angle, thus had a 90° hydrogel edge face. These Examples were laminated to TEGADERM/adhesive film, rolled with weighted roller and aged for 2 weeks at 24° C. 50% RH or in a 50° C. oven. A total of 10 samples were tested on PET coated with LOPAREX 6300A release coating and another 10 samples were tested on PET coated with LOPAREX 164Z release coating, both were constructed with and without the tapered edge. The gel was cut to 2.54×2.54 cm square. T-Peel test results for Examples E3-E4, after storage under the given conditions are shown in Tables 4 and 5, below.

TABLE 4

| Example | E2 24° C./ 50% RH | C4 24° C./ 50% RH | E2 50° C. | C4 50° C. |
|---|---|---|---|---|
| Liner 6300 Ave* Peak Force | 2.21 | 3.66 | 5.90 | 8.81 |
| Liner 6300 Max Peal Force | 6.07 | 4.65 | 9.60 | 13.54 |
| Liner 164Z Ave* Peak Force | 1.05 | 1.43 | 4.87 | 13.49 |
| Liner 164Z Max Peal Force | 1.80 | 3.04 | 6.76 | 21.3 |

*Average of 10 samples

The results in Table 4 demonstrate a significant improvement in lowered maximum peel forces required to remove the gel liner from the dressing.

Examples E3-E4

An alternative method of preparing a tapered edge hydrogel adhesive was developed. The hydrogel material as prepared in Example 1 was extruded at 50 to 60 mils (0.127 to 0.152 cm) between release liner and calendar. Depression bands were made using a 1 cm wide band of tape applied onto one calendaring roll at a thickness of 40-50 mils (0.102 to 0.127 cm) to create a thin region in the hydrogel. This thin region was either slit down the middle to create a thin tongue or step of hydrogel continuing beyond the taper, as shown in FIG. 6a, for Example E3 or cut at the end of the sloping edge of the hydrogel to produce a tapered hydrogel edge with no tongue or step, for Example E4, as shown in FIG. 6c. The amount of gel in the thin regions was greater than what would be expected. Rather than being 10-20 mils (0.025 to 0.051 cm) thickness, the regions were actually thicker due to the visco-elastic nature of the extruded material.

Comparative Example C5

Another hydrogel adhesive Comparative Example C5 was prepared in the same manner as C1 and C4, above, with no taper.

The gels of Examples E3-E4 and C5 were cut at 3 cm widths and constructed as shown below, with 5 mm of the thin step of hydrogel included or cut off the sample. Test samples were constructed on 2 mil (51 micrometer) PET coated with LOPAREX 7300 or 2 mil (51 micrometer) PET coated with LOPAREX 164Z release liner. Samples were placed in a 50° C. oven for 2 weeks and T-peel tested (6 inches (15.24 cm) per min jaw speed) to determine the maximum peel force to remove the liner.

TABLE 5

| Example | C5 No Taper | E3 Tapered with step | E4 Tapered with no edge |
|---|---|---|---|
| Liner 7300 Ave* Peak Force | 7.92 | 3.89 | 2.78 |
| Liner 7300 Max Peal Force | 17.13 | 15.66 | 6.45 |
| Liner 164Z Ave* Peak Force | 11.76 | 5.89 | 4.18 |
| Liner 164Z Max Peal Force | 22.95 | 13.05 | 6.36 |

*Average of 40 samples

As various changes could be made in the above constructions, compositions and methods without departing from the scope of the invention as defined in the claims, it is intended that all matter contained in the above description or shown in the accompanying drawings be interpreted as illustrative and not in a limiting sense. The Examples described in this application are illustrative of the possibilities of varying the type, quantity and ratio of composition as well as the methods for making formulations of the present invention. The complete disclosures of all patents, patent applications, and publications recited herein are incorporated by reference, as if individually incorporated by reference.

What is claimed is:

1. An island dressing, comprising
a backing that comprises a first major surface;
an adhesive located on the first major surface of the backing;
an adhesive hydrogel island pad proximate the first major surface of the backing wherein the hydrogel pad comprises less than 45% water; and
a release liner;
wherein at least a portion of the perimeter of the hydrogel pad is tapered to a stepped edge, and wherein the thickness of the tapered portion of the hydrogel pad is reduced by 0.020 inches or more such that the thickness of the hydrogel pad at the stepped edge is 0.010 inches or more to create an air gap between the stepped edge of the hydrogel pad, the backing layer and the liner.

2. An island dressing, comprising
a backing that comprises a first major surface;
an adhesive located on the first major surface of the backing;
an adhesive hydrogel island pad proximate the first major surface of the backing; and
a release liner;
wherein at least a portion of the perimeter of the hydrogel pad is tapered to a stepped edge; and wherein the thickness of the tapered portion of the hydrogel pad is reduced by 0.020 inches or more such that the thickness of the hydrogel pad at the stepped edge is 0.010 inches or more to create an air gap between the stepped edge of the hydrogel pad, the backing layer and the liner;
wherein the average maximum peel force to initiate separation of an one-inch wide untapered hydrogel pad and a release liner is at least 25% greater than the average maximum peel force of the tapered hydrogel pad and the release liner, when measured by the T-peel Test Method performed after conditioning the island dressing for one week at 50 degrees C.

3. An island dressing, comprising
a backing that comprises a first major surface;
an adhesive located on the first major surface of the backing;
an adhesive hydrogel island pad proximate the first major surface of the backing; and
a release liner;

wherein at least a portion of the perimeter of the hydrogel pad is tapered to a stepped edge and wherein the thickness of the tapered portion of the hydrogel pad is reduced by 0.020 inches or more such that the thickness of the hydrogel pad at the stepped edge is 0.010 inches or more to create an air gap between the stepped edge of the hydrogel pad, the backing layer and the liner.

4. The island dressing of claim 1, wherein the hydrogel pad is attached to the adhesive on the first major surface of the backing.

5. The island dressing of claim 1, further comprising a carrier releasably attached to a second major surface of the backing.

6. The island dressing of claim 1, wherein the hydrogel comprises
   a first polymer comprising a cross-linked poly (N-vinyl) lactam;
   a swelling agent; and
   a second modifying polymer swellable in the swelling agent;
   wherein the first polymer forms a pressure sensitive adhesive in the presence of the swelling agent; and
   wherein the second modifying polymer and the swelling agent reduce the adhesiveness of the first polymer while at least maintaining the cohesion of the composition.

7. The island dressing of claim 1, wherein the backing comprises a transparent or translucent polymeric film.

8. The island dressing of claim 1, wherein the hydrogel is transparent or translucent.

9. The island dressing of claim 1, further comprising an antimicrobial agent.

10. The island dressing of claim 9, wherein the antimicrobial agent is selected from the group consisting of parachlorometaxylenol; triclosan; chlorhexidine and salts thereof; poly hexamethylene biguanide and salts thereof; iodine; idodophors; silver oxide; silver and its salts; peroxides; antibiotics; and combinations of the foregoing.

11. The island dressing of claim 6 wherein the poly (N-vinyl)lactam is selected from the group consisting of poly N-vinyl-2-pyrrolidone, poly N-vinyl-2-valerolactam, poly N-vinyl-2-caprolactam, and combinations of the foregoing.

12. The island dressing of claim 6 wherein the swelling agent is selected from the group consisting of monohydric alcohols; polyhydric alcohols; glycerol; polyglycerols; sorbitol; polyhydric alcohol ethoxylates; methoxides of polyethylene glycol; methoxides of polyhydric alcohol ethoxylates; and combinations of the foregoing.

13. The island dressing of claim 6, wherein the swelling agent is greater than 50% of the total weight of the composition.

14. The island dressing of claim 6, wherein the second modifying polymer comprises a polysaccharide, polysaccharide derivatives, acrylate, acrylate derivatives, cellulose, cellulose derivatives, and combinations thereof.

15. The island dressing of claim 14 wherein the modifying polymer is selected from the group consisting of hydroxypropyl guar; guar gum; hydroxyethyl cellulose; hydroxypropyl cellulose; hydroxypropyl methylcellulose; polymeric quaternary ammonium salt of hydroxyethyl cellulose reacted with trialkyl ammonium substituted epoxide; copolymers of hydroxyethyl cellulose and diallyldimethyl ammonium chloride; and derivatives and combinations of the foregoing.

16. The island dressing of claim 6 wherein: the first polymer is present in the composition in an amount between 5% and 45% by weight; the swelling agent is present in an amount of at least 55% by weight; and the second modifying polymer is present in an amount between 0.1% and 40% by weight.

17. The island dressing of claim 6 wherein first polymer is poly N-vinyl-2-pyrrolidone; the swelling agent is triglycerol; the second polymer is selected from the group consisting of hydroxypropyl guar; guar gum; hydroxyethyl cellulose; hydroxypropyl cellulose; hydroxypropyl methylcellulose; polymeric quaternary ammonium salt of hydroxyethyl cellulose reacted with trialkyl ammonium substituted epoxide; copolymers of hydroxyethyl cellulose and diallyldimethyl ammonium chloride; and derivatives and combinations of the foregoing; and the antimicrobial agent is chlorhexidine gluconate.

18. An island dressing, comprising
   a backing that comprises a first major surface;
   an adhesive located on the first major surface of the backing;
   an adhesive hydrogel island pad proximate the first major surface of the backing, wherein the hydrogel pad comprises less than 45% water; and
   a release liner;
   wherein at least a portion of the perimeter of the hydrogel pad is tapered to a stepped edge; and wherein the thickness of the tapered portion of the hydrogel pad is reduced by 0.020 inches or more such that the thickness of the hydrogel pad at the stepped edge is 0.010 inches or more to create an air gap between the stepped edge of the hydrogel pad, the backing layer and the liner;
   wherein the adhesive hydrogel comprises:
   a first polymer comprising a cross-linked poly (N-vinyl) lactam present in the composition in an amount between 5% and 50% by weight, wherein the cross-linked poly (N-vinyl lactam) has a Swelling Capacity of at least 15 milliliters of water per gram of the cross-linked poly(N-vinyl lactam), and is selected from the group consisting of poly N-vinyl-2-pyrrolidone, poly N-vinyl-2-valerolactam, poly N-vinyl-2-caprolactam, and combinations of the foregoing;
   a swelling agent present in an amount of at least 50% by weight, wherein the swelling agent is selected from the group consisting of polyhydric alcohols; glycerol; polyglycerols; sorbitol; polyhydric alcohol ethoxylates; methoxides of polyethylene glycol; methoxides of polyhydric alcohol ethoxylates; and combinations of the foregoing; and
   a second modifying polymer swellable in the swelling agent, and present in an amount between 0.1% and 40% by weight, wherein the second modifying polymer is selected from the group consisting of hydroxypropyl guar; guar gum; hydroxyethyl cellulose; hydroxypropyl cellulose; hydroxypropyl methylcellulose; polymeric quaternary ammonium salt of hydroxyethyl cellulose reacted with trialkyl ammonium substituted epoxide; copolymers of hydroxyethyl cellulose and diallyldimethyl ammonium chloride; and derivatives and combinations of the foregoing;
   wherein the first polymer forms a pressure sensitive adhesive in the presence of the swelling agent; and
   wherein the second modifying polymer and the swelling agent reduce the adhesiveness of the first polymer while at least maintaining the cohesion of the composition.

19. An island dressing, comprising
   a backing that comprises a first major surface;
   an adhesive located on the first major surface of the backing;
   an adhesive hydrogel island pad proximate the first major surface of the backing; and
   a release liner;

wherein at least a portion of the perimeter of the hydrogel pad is tapered to a stepped edge; and wherein the thickness of the tapered portion of the hydrogel pad is reduced by 0.020 inches or more such that the thickness of the hydrogel pad at the stepped edge is 0.010 inches or more to create an air gap between the stepped edge of the hydrogel pad, the backing layer and the liner;

wherein the average maximum peel force to initiate separation of an one-inch wide untapered hydrogel pad and a release liner is at least 25% greater than the average maximum peel force of the tapered hydrogel pad and the release liner, when measured by the T-peel Test Method performed after conditioning the island dressing for one week at 50 degrees C.; and wherein the hydrogel comprises:

a first polymer comprising a cross-linked poly (N-vinyl) lactam present in the composition in an amount between 5% and 50% by weight, wherein the cross-linked poly (N-vinyl lactam) has a Swelling Capacity of at least 15 milliliters of water per gram of the cross-linked poly(N-vinyl lactam), and is selected from the group consisting of poly N-vinyl-2-pyrrolidone, poly N-vinyl-2-valerolactam, poly N-vinyl-2-caprolactam, and combinations of the foregoing;

a swelling agent present in an amount of at least 50% by weight, wherein the swelling agent is selected from the group consisting of polyhydric alcohols; glycerol; polyglycerols; sorbitol; polyhydric alcohol ethoxylates; methoxides of polyethylene glycol; methoxides of polyhydric alcohol ethoxylates; and combinations of the foregoing; and a second modifying polymer swellable in the swelling agent, and present in an amount between 0.1% and 40% by weight, wherein the second modifying polymer is selected from the group consisting of hydroxypropyl guar; guar gum; hydroxyethyl cellulose; hydroxypropyl cellulose; hydroxypropyl methylcellulose; polymeric quaternary ammonium salt of hydroxyethyl cellulose reacted with trialkyl ammonium substituted epoxide; copolymers of hydroxyethyl cellulose and diallyldimethyl ammonium chloride; and derivatives and combinations of the foregoing;

wherein the first polymer forms a pressure sensitive adhesive in the presence of the swelling agent; and wherein the second modifying polymer and the swelling agent reduce the adhesiveness of the first polymer while at least maintaining the cohesion of the composition.

20. An island dressing, comprising
a backing that comprises a first major surface;
an adhesive located on the first major surface of the backing;
an adhesive hydrogel island pad proximate the first major surface of the backing; and
a release liner;

wherein at least a portion of the perimeter of the hydrogel pad is tapered to a stepped edge; and wherein the thickness of the tapered portion of the hydrogel pad is reduced by 0.020 inches or more such that the thickness of the hydrogel pad at the stepped edge is 0.010 inches or more to create an air gap between the stepped edge of the hydrogel pad, the backing layer and the liner;

wherein the hydrogel comprises:

a first polymer comprising a cross-linked poly (N-vinyl) lactam present in the composition in an amount between 5% and 50% by weight, wherein the cross-linked poly (N-vinyl lactam) has a Swelling Capacity of at least 15 milliliters of water per gram of the cross-linked poly(N-vinyl lactam), and is selected from the group consisting of poly N-vinyl-2-pyrrolidone, poly N-vinyl-2-valerolactam, poly N-vinyl-2-caprolactam, and combinations of the foregoing;

a swelling agent present in an amount of at least 50% by weight, wherein the swelling agent is selected from the group consisting of polyhydric alcohols; glycerol; polyglycerols; sorbitol; polyhydric alcohol ethoxylates; methoxides of polyethylene glycol; methoxides of polyhydric alcohol ethoxylates; and combinations of the foregoing; and a second modifying polymer swellable in the swelling agent, and present in an amount between 0.1% and 40% by weight, wherein the second modifying polymer is selected from the group consisting of hydroxypropyl guar; guar gum; hydroxyethyl cellulose; hydroxypropyl cellulose; hydroxypropyl methylcellulose; polymeric quaternary ammonium salt of hydroxyethyl cellulose reacted with trialkyl ammonium substituted epoxide; copolymers of hydroxyethyl cellulose and diallyldimethyl ammonium chloride; and derivatives and combinations of the foregoing;

wherein the first polymer forms a pressure sensitive adhesive in the presence of the swelling agent; and wherein the second modifying polymer and the swelling agent reduce the adhesiveness of the first polymer while at least maintaining the cohesion of the composition.

21. An island dressing according to claim 1, wherein the thickness of the tapered portion of the hydrogel pad is reduced by up to 0.040 inches.

22. An island dressing according to claim 1, wherein the thickness of the hydrogel pad at the stepped edge is 0.020 inches or less.

23. An island dressing according to claim 1, wherein the thickness of the hydrogel pad at the stepped edge is 0.030 inches or less.

24. An island dressing according to claim 1, wherein the thickness of the hydrogel pad at the stepped edge is 0.040 inches or less.

25. An island dressing according to claim 1, wherein the tapered portion of the hydrogel pad tapers from a thickness of 0.40 inches or more to the stepped edge.

26. An island dressing according to claim 1, wherein the tapered portion of the hydrogel pad tapers from a thickness of 0.50 inches or more to the stepped edge.

27. An island dressing according to claim 1, wherein the tapered portion of the hydrogel pad tapers from a thickness of 0.40 inches or more to the stepped edge, and wherein the thickness of the hydrogel pad at the stepped edge is 0.030 inches or less.

28. An island dressing according to claim 27, wherein the thickness of the hydrogel pad at the stepped edge is 0.020 inches or less.

29. An island dressing according to claim 2, wherein the thickness of the tapered portion of the hydrogel pad is reduced by up to 0.040 inches.

30. An island dressing according to claim 2, wherein the thickness of the hydrogel pad at the stepped edge is 0.020 inches or less.

31. An island dressing according to claim 2, wherein the thickness of the hydrogel pad at the stepped edge is 0.030 inches or less.

32. An island dressing according to claim 2, wherein the thickness of the hydrogel pad at the stepped edge is 0.040 inches or less.

33. An island dressing according to claim 2, wherein the tapered portion of the hydrogel pad tapers from a thickness of 0.40 inches or more to the stepped edge.

34. An island dressing according to claim 2, wherein the tapered portion of the hydrogel pad tapers from a thickness of 0.50 inches or more to the stepped edge.

35. An island dressing according to claim 2, wherein the tapered portion of the hydrogel pad tapers from a thickness of 0.40 inches or more to the stepped edge, and wherein the thickness of the hydrogel pad at the stepped edge is 0.030 inches or less.

36. An island dressing according to claim 35, wherein the thickness of the hydrogel pad at the stepped edge is 0.020 inches or less.

37. An island dressing according to claim 3, wherein the thickness of the tapered portion of the hydrogel pad is reduced by up to 0.040 inches.

38. An island dressing according to claim 3, wherein the thickness of the hydrogel pad at the stepped edge is 0.020 inches or less.

39. An island dressing according to claim 3, wherein the thickness of the hydrogel pad at the stepped edge is 0.030 inches or less.

40. An island dressing according to claim 3, wherein the thickness of the hydrogel pad at the stepped edge is 0.040 inches or less.

41. An island dressing according to claim 3, wherein the tapered portion of the hydrogel pad tapers from a thickness of 0.40 inches or more to the stepped edge.

42. An island dressing according to claim 3, wherein the tapered portion of the hydrogel pad tapers from a thickness of 0.50 inches or more to the stepped edge.

43. An island dressing according to claim 3, wherein the tapered portion of the hydrogel pad tapers from a thickness of 0.40 inches or more to the stepped edge, and wherein the thickness of the hydrogel pad at the stepped edge is 0.030 inches or less.

44. An island dressing according to claim 43, wherein the thickness of the hydrogel pad at the stepped edge is 0.020 inches or less.

\* \* \* \* \*